United States Patent
Beutler et al.

(10) Patent No.: US 9,599,667 B1
(45) Date of Patent: Mar. 21, 2017

(54) VISIBLE LIGHT LASER VOLTAGE PROBING ON THINNED SUBSTRATES

(71) Applicant: Sandia Corporation, Albuquerque, NM (US)

(72) Inventors: Joshua Beutler, Albuquerque, NM (US); John Joseph Clement, Albuquerque, NM (US); Mary A. Miller, Albuquerque, NM (US); Jeffrey Stevens, Albuquerque, NM (US); Edward I. Cole, Jr., Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/836,713

(22) Filed: Aug. 26, 2015

Related U.S. Application Data

(60) Provisional application No. 62/043,505, filed on Aug. 29, 2014.

(51) Int. Cl.
| | |
|---|---|
| *G01N 21/00* | (2006.01) |
| *G01R 31/311* | (2006.01) |
| *H01L 21/66* | (2006.01) |
| *H01L 21/3065* | (2006.01) |

(Continued)

(52) U.S. Cl.
CPC ....... *G01R 31/311* (2013.01); *G01N 21/9501* (2013.01); *H01L 21/3065* (2013.01); *H01L 21/67253* (2013.01); *H01L 22/20* (2013.01)

(58) Field of Classification Search
CPC ...... G02B 21/33; G02B 7/028; G02B 21/002; G02B 21/02; G02B 21/248; G02B 21/28; G02B 27/58; G02B 7/023; G02B 7/16; G01N 21/9501; G01N 21/956;

(Continued)

(56) References Cited

U.S. PATENT DOCUMENTS

| | | | |
|---|---|---|---|
| 7,616,312 B2 | 11/2009 | Kasapi et al. | |
| 8,394,244 B1 * | 3/2013 | Patterson | H01L 21/67086 204/192.34 |
| 2012/0249859 A1 | 10/2012 | Niu et al. | |

(Continued)

OTHER PUBLICATIONS

Kindereit, Ulrike, "Fundamentals and Future Applications of Laser Voltage Probing", IEEE Reliability Physics Symposium, pp. 1-11, Jun. 2014.

(Continued)

*Primary Examiner* — Michael P Stafira
(74) *Attorney, Agent, or Firm* — Medley, Behrens & Lewis, LLC

(57) ABSTRACT

The various technologies presented herein relate to utilizing visible light in conjunction with a thinned structure to enable characterization of operation of one or more features included in an integrated circuit (IC). Short wavelength illumination (e.g., visible light) is applied to thinned samples (e.g., ultra-thinned samples) to achieve a spatial resolution for laser voltage probing (LVP) analysis to be performed on smaller technology node silicon-on-insulator (SOI) and bulk devices. Thinning of a semiconductor material included in the IC (e.g., backside material) can be controlled such that the thinned semiconductor material has sufficient thickness to enable operation of one or more features comprising the IC during LVP investigation.

20 Claims, 4 Drawing Sheets

(51) Int. Cl.
*H01L 21/67* (2006.01)
*G01N 21/95* (2006.01)

(58) Field of Classification Search
CPC ....... G01N 2021/1719; G01N 21/1717; G01N 21/41; G01N 21/06
See application file for complete search history.

(56) References Cited

U.S. PATENT DOCUMENTS

2015/0002182 A1* 1/2015 Eiles .................. G01R 31/2656
324/762.01

OTHER PUBLICATIONS

Boit, et al., "Physical IC debug—backside approach and nanoscale challenge", Advances in Radio Science, vol. 6, pp. 265-272, 2008.
Vigil, et al., "Integrated Circuit Super-Resolution Failure Analysis with Solid Immersion Lenses", Electronic Device Failure Analysis, vol. 16 Issue 2, pp. 26-32, 2014.

* cited by examiner

VISIBLE LIGHT LASER VOLTAGE PROBING ON THINNED SUBSTRATES

RELATED APPLICATION

This application claims priority to U.S. Provisional Patent Application No. 62/043,505, filed on Aug. 29, 2014, entitled "VISIBLE LIGHT LVP ON ULTRA-THINNED SUBSTRATES", the entirety of which is incorporated herein by reference.

STATEMENT OF GOVERNMENTAL INTEREST

This invention was developed under contract DE-AC04-94AL85000 between Sandia Corporation and the U.S. Department of Energy. The U.S. Government has certain rights in this invention.

BACKGROUND

Laser Voltage Probing (LVP) is an optical tool for failure analysis and real time characterization and/or logic debugging of electrical signals propagating at operational speeds through an integrated circuit (IC). Conventional LVP systems rely on free carrier index changes and free carrier absorption within semiconductors. Infrared wavelengths are used to take advantage of silicon's relative transparency for backside probing. The incident light is reflected back, captured, detected, and amplified. The small modulations in reflected light intensity resulting from carrier density changes with electric field are utilized to determine local transistor logic states as a function of time.

With the continual reduction of IC feature sizes (e.g., a trace, a transistor, a CMOS transistor, a diode, a PN junction or other semiconductor component or device that transfers or conveys free carriers or conducting current, etc.), backside, laser-based failure analysis tools are limited in spatial resolution by the refraction limits of infrared light and the relatively long wavelengths required for through-silicon probing. Even with state of the art solid immersion lenses (SILs), modern 22 nanometer (nm) devices are at and past the limit of practical resolution for LVP systems utilizing infrared light.

SUMMARY

The following is a brief summary of subject matter that is described in greater detail herein. This summary is not intended to be limiting as to the scope of the claims.

Various technologies presented herein relate to utilizing visible light for laser voltage probing (LVP) of an integrated circuit (IC). To enable visible light to pass through a backside of an IC and be incident upon one or more features included in the IC, a substrate of the IC can be thinned to enable probing of the feature(s) with the visible light via the backside of the IC, and further, enable reflection of the visible light from a surface of the feature(s) (back through the substrate) to a detector. The material forming the backside of the IC, e.g., a semiconductor, can be thinned to a thickness such that while the feature can be probed by the visible light, the IC can remain operational throughout the LVP operation. The thinned material can have a thickness so that the shorter, visible wavelengths can pass through the thinned material both in the incident and reflected directions.

Thinning of the semiconductor material can be controlled such that at least a portion of the insulating layer remains to enable operation of the IC during testing. Thinning (e.g., die thinning) of the semiconductor material can be performed by any suitable material removal technique. In a non-exhaustive list, such techniques include reactive ion-etching processing, focused ion beam (FIB), gas-assisted FIB, pulse laser-assisted etching, xenon difluoride ($XeF_2$) etching, etc. Fabrication of the IC can be such that an insulating layer (e.g., a buried oxide (BOX) layer) has been formed over the one or more features included in the IC.

The semiconductor substrate material can be thinned and/or the insulating layer (if present) or it can be thinned to a thickness of about 2-4 microns ($\mu m$), of about 3-4 $\mu m$'s, of about 2 $\mu m$'s, of about 0.25 $\mu m$'s, of about 60-70 nanometers, of about 5 nanometers, and/or a distance of 2-4 times a wavelength of the incident light, between an exposed surface of the semiconductor material and a surface of the feature. Further, the semiconductor material can be thinned to a minimum thickness at which the IC is still operational, and during which, the visible light (incident light and reflected light) can pass through the semiconductor material to enable LVP of the IC.

The visible light can be generated by a laser and have a wavelength of about 650 nanometers (nm), of about 510 nm, of about 475 nm, a value in a range of about 400-700 nm, or a value in a range of about 633-640 nm.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
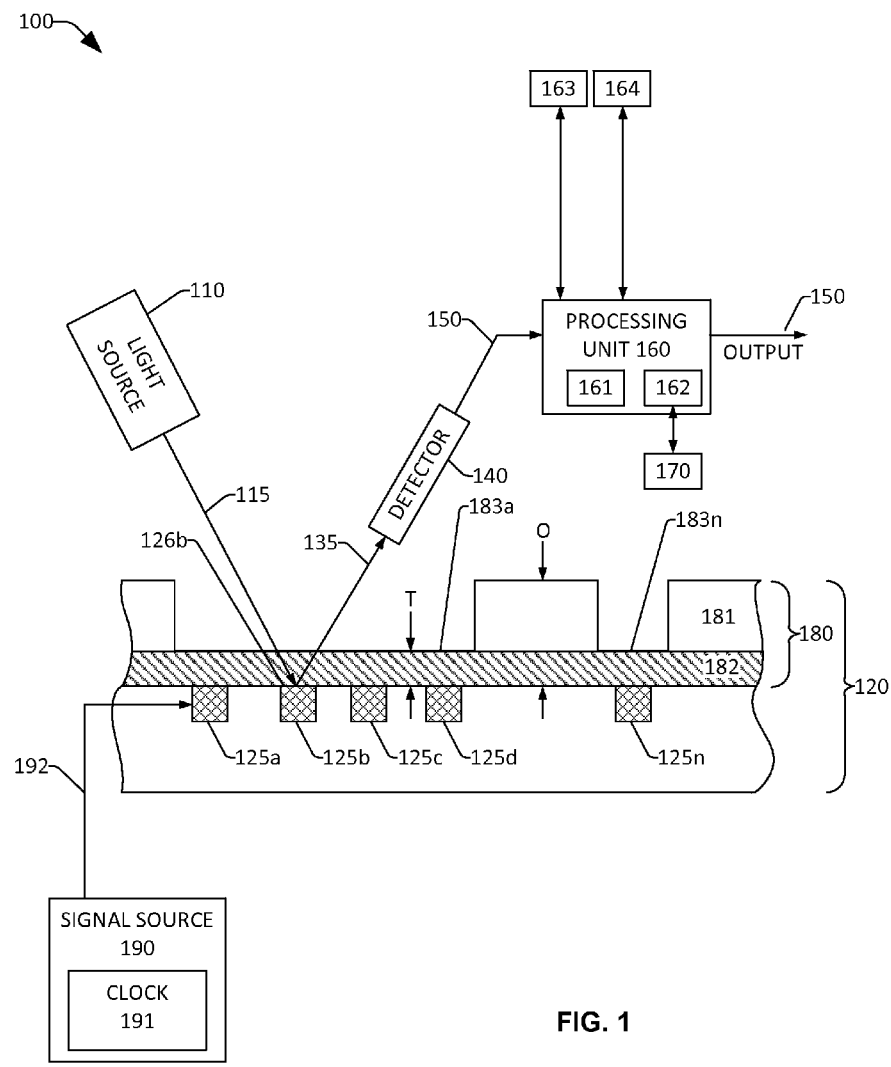
FIG. 1 illustrates an LVP system utilizing visible light, according to an embodiment.

Various technologies pertaining to utilizing visible light in conjunction with a thinned structure to enable characterization of operation of one or more features included in an integrated circuit (IC), are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. The terms "component" and "system" are also intended to encompass hardware configured to cause certain functionality to be performed, where such hardware can include, but is not limited to including, Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Further, the term "or" is intended to mean an inclusive "or" rather than an exclusive "or". That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

As previously mentioned, as IC devices have reduced in size with an according reduction in feature sizes (e.g., a trace, a transistor, a CMOS transistor, a diode, a PN junction or other semiconductor component or device that transfers or conveys free carriers or conducting current, etc.), conventional backside, laser-based failure analysis tools utilizing longer wavelength light (e.g., infrared) have become limited in their ability to resolve spatial resolution owing to refraction limits of the light and the relatively long wavelengths required for through-silicon probing.

The various embodiments presented herein address the spatial resolution limit when utilizing infrared light, wherein one or more embodiments utilize LVP with electromagnetic waves having a shorter wavelength, e.g., light waves in the visible wavelength portion of the electromagnetic spectrum. In one or more embodiments, thinning (e.g., backside thinning, backside ultra-thinning, ultra-thinning, etc.) of a semiconductor material (e.g., in a silicon on insulator (SOI) device) is utilized. The semiconductor material of the device is thinned to a sufficient extent such that shorter, visible wavelengths can be used for LVP analysis, thus enabling improved spatial resolution and enhanced LVP signals, when compared to an infrared based LVP system.

FIG. 1 illustrates a system 100, whereby the system 100 can be a LVP system configured to utilize electromagnetic radiation from the visible portion of the electromagnetic spectrum to analyze at least one IC.

The system 100 includes a light source 110 configured to generate and emit light 115 onto an IC device 120, wherein the light 115 has a wavelength in the visible portion of the electromagnetic spectrum. At least one feature 125a-n is included in the IC device 120, where n is an integer greater than one. As shown, the light 115 is incident upon a surface of a respective feature 125a-n, e.g., feature 125b, and is reflected from the surface (e.g., surface 126b) of the feature 125b. The system 100 further comprises a detector 140, which is located to detect (capture) the reflected light 135 being reflected from the feature 125b. The detector 140 is configured to generate a test signal 150 based upon the reflected light 135 (e.g., via electro-optical conversion). The system 100 also comprises a processing unit 160, which includes a processor 161 and memory 162, where the memory 162 comprises instructions that are executed by the processor 161. The processing unit 160 receives the test signal 150 generated by the detector 140.

The system 100 also comprises a spectrum analyzer 163 and an oscilloscope 164, which are in communication with the processing unit 160. In an embodiment, the processing unit 160 forwards the test signal 150 to the spectrum analyzer 163, and the spectrum analyzer 163 can generate a laser voltage image that shows particular features in the IC 120 based upon a particular criteria. For example, a laser voltage image can be presented where only those transistors that are switching at 10 MHz are shown (e.g., as a bright region on the laser voltage image) and all other regions of the IC undergoing LVP are dark. In another embodiment, the processing unit 160 supplies the test signal 150 to the oscilloscope 164. The oscilloscope 164 can create a waveform (using averaging techniques) that is indicative of a waveform of an electrical signal passing through the IC 120 during the LVP operation.

In an embodiment, the memory 162 includes a base signal 170. In response to the test signal 150 being received at the processing unit 160, the processing unit 160 is further configured to compare the test signal 150 (e.g., as a laser voltage image or as a waveform) with the base signal 170. The base signal 170 can be a signal captured for a known operation of the IC 120 and features 125a-n. For example, the base signal 170 was captured during an LVP operation conducted on an IC having a known structure, operation, performance, etc., wherein comparison of the test signal 150 with the base signal 170 enables operation of the IC 120 and features 125a-n to be established and any further troubleshooting to be undertaken based thereon, e.g., to determine whether any of the features 125a-n (e.g., a transistor) is defective. The base signal 170 can also be derived from a design file, or other suitable source.

As shown in FIG. 1, the IC device 120 can comprise a layer of semiconductor material 180, which, in an embodiment, the semiconductor material 180 can be silicon-based. Depending upon how the IC device 120 has been fabricated, the semiconductor material can be processed such that there is a silicon substrate 181 in which an insulating layer 182 has been formed. For example, the insulating layer 182 is a buried oxide (BOX) layer formed between the layer of semiconductor material 180 and the plurality of features 125a-n. The semiconductor material 180 can be thinned in one or more regions 183a-183n from an original thickness O to a thinned thickness T. As shown, the thinned regions 183a-183n can have a width such that a plurality of features (e.g., features 125a-d) are able to be exposed to the light 115 or a single feature (e.g., feature 125n) is able to be exposed to the light 115.

The thickness T can be a function of a wavelength of the light 115 being utilized to illuminate the device 120. For example, if the light 115 is from the red portion of the visible spectrum (e.g., having a wavelength in a range of about 620-750 nm), T≈about 3-4 µm's. In another example, if the light 115 is from the green portion of the visible spectrum (e.g., having a wavelength in a range of about 495-570 nm), T≈about 2 µm's. In a further example, if the light 115 is from the blue portion of the visible spectrum (e.g., having a wavelength in a range of about 450-495 nm), T≈about 5 nm's. Removal of material from the semiconductor can be controlled such that T has a thickness such that it is transparent to the incident light 115, and further, the reflected light 135 is able to pass through the thinned semiconductor material such that the reflected light 135 received at the detector 140 has an intensity that it is possible to discern an effect (e.g., modulation) imparted on the light incident (e.g., incident light 115) at the feature 125 as a result of interaction with the feature 125 and an electrical signal passing therethrough. Further, while enabling transmission (e.g., of the incident light 115) and reflection (e.g., of the reflected light 135) of light through the thinned semiconductor material, the thickness T of the thinned semiconductor material is sufficient to enable operation of the IC device 120 during respective transmission/reflection of the light 115 and 135. It is possible to thin the semiconductor material to as little as 60-70 nanometers (nm) and still have sufficient material to enable operation of the IC 120 during testing. Hence, the only limit to the thickness of the semiconductor material at regions 183a-183n is there is sufficient semiconductor material for the IC 120 to remain functional during the LVP operation.

The system 100 also comprises a signal source 190 and a clock 191, where the signal source 190 can generate an electrical signal 192 based upon the clock 191. The electrical signal 192 can be any signal suitable to enable testing of the IC device 120, e.g., the electrical signal 192 can be a clocked signal, a square wave, a sine wave, etc. The electrical signal 192 can be applied to the IC device 120, e.g., to power the one or more features 125a-n. For example, the feature 125a can be a transistor, such that as the transistor 125a is being powered by the electrical signal 192, an associated change in the electrical signal 192 and/or the transistor 125a resulting from operation of the transistor 125a during application of the electrical signal 192 can affect the intensity, waveform, etc., of the reflected light 135 as a result of the operation of the transistor 125a affecting the incident light 115. For example, during application of the electrical signal 192 at the transistor 125a, optical absorption of generated free carriers and or changes in refractive index due to the presence of free carriers 125a creates a modulation between the incident light 115 and the reflected light 135. In an embodiment, the processing unit 160 can determine a local transistor logic state at the transistor 125a, as a function of time, based upon the modulations. Thus, real time logic debugging of an electrical signal 192 propagating at an operational speed(s) through the IC 120 can be achieved. The modulation of the incident light 115 by one or more effects engendered at the feature 125a causes the reflected light 135 to have at least one characteristic different to the incident light, e.g., the reflected light 135 has a different amplitude, waveform, magnitude, etc., to the incident light 115.

With reference to the detector 140, any suitable detector can be utilized, such as a silicon-based detector, a photodiode, a silicon-based photodiode, and avalanche photodiode (APD), photo-multiplier tube, etc. For example, the detector 140 can be an APD, wherein the APD can be a high gain, low noise APD.

The light source 110 can be any suitable device, such as a laser emitting light at a desired wavelength, e.g., red light, green light, blue light, etc., wherein the light can be collimated. For example, a helium-neon (HeNe) laser operating at 633 nm, 5 millwatts (mW), with approximately 500 microwatts (µW) power on the feature surface 126. In an embodiment, the IC device 120 can be a buffer amplifier on a 350 nm technology operating at with an electrical signal of 3.3 volts (V).

The detector 140 can generate the test signal 150, and suitable circuitry (not shown) can amplify the test signal 150 prior to the processing unit 160 receiving the test signal 150. In an embodiment, the processing unit 160 can utilize a spectrum analyzer 163 to analyze the test signal 150. In a first embodiment, the processing unit 160 can be configured (e.g., in conjunction with the spectrum analyzer 163, or any other frequency discriminating device, e.g., a lock in amplifier) to identify a harmonic (e.g., a primary harmonic) in the test signal 150, wherein the harmonic can be present as a spectral peak in the test signal 150 resulting, for example, from the clocking frequency of the clock utilized to generate the electrical signal 192. The processing unit 160 in conjunction with the spectrum analyzer 163 can be further utilized for imaging of the IC 120 and features 125a-n, e.g., laser voltage imaging (LVI), with the visible light 115. During such imaging, the spectrum analyzer 163 can be configured with a zero span set at a frequency of the spectral peak, as previously identified.

Thinning (e.g., die thinning) of the semiconductor 180, from an original thickness O to a thinned thickness T, to form the thinned regions 183a-n can be performed by any suitable material removal technique. In a non-exhaustive list, such techniques include reactive ion-etching processing, focused ion beam (FIB), gas-assisted FIB, pulse laser-assisted etching, xenon difluoride ($XeF_2$) etching, etc. In an embodiment, a coarse material removal technique can be initially utilized with a fine material removal technique being applied as a final stage operation to achieve thinning of the semiconductor material 180 to the desired thickness T. In a further embodiment where the semiconductor layer 180 comprises a silicon semiconductor layer 181 and an insulating layer 182, the thinning operation can be configured such that the semiconductor layer 181 is preferentially removed by the thinning operation, while the insulating layer 182 is resistant to the thinning operation, therein enabling removal of only the semiconductor layer 181 with retention of the insulating layer 182. In another embodiment the semiconductor layer 180 and a portion of the insulating layer 182 can be removed until a desired thickness of insulating layer 182 remains. A process for removal and thinning of the semiconductor layer 181 can comprise a milling process, followed by a pulse laser tool, and finally a reactive ion-etch to achieve the desired thickness.

The various components and devices included in the system 100 (or a portion thereof) can be incorporated into a laser scanning microscope. Further, the light source 110 can operate in conjunction with operation of the spectrum analyzer 163 and the oscilloscope 164, wherein the light source 110 can be scanned over the feature 125 during generation of a laser voltage image, and can be pointed at a particular location (e.g., feature 125a) and obtain a test signal 150 from the detector 140 when the light source is utilized in a spot manner.

It is to be appreciated that while not shown a plurality of lenses can be utilized with the system 100. For example, while system 100 is illustrated with no lens present in the light path(s) of incident light 115 and/or reflected light 135 (e.g., operating with an air gap), any suitable lens can be utilized, such as an oil immersion lens, a solid immersion lens (SIL), etc. Hence, the system can be designed in accordance with a desired resolution, D, per eqn. 1:

$$D = \frac{0.61\lambda}{NA} \quad (1)$$

where D is the minimum resolution limit of two points, $\lambda$ is the wavelength of the light being utilized in the LVP process, and NA is the numerical aperture of a microscope objective.

Figure 2:
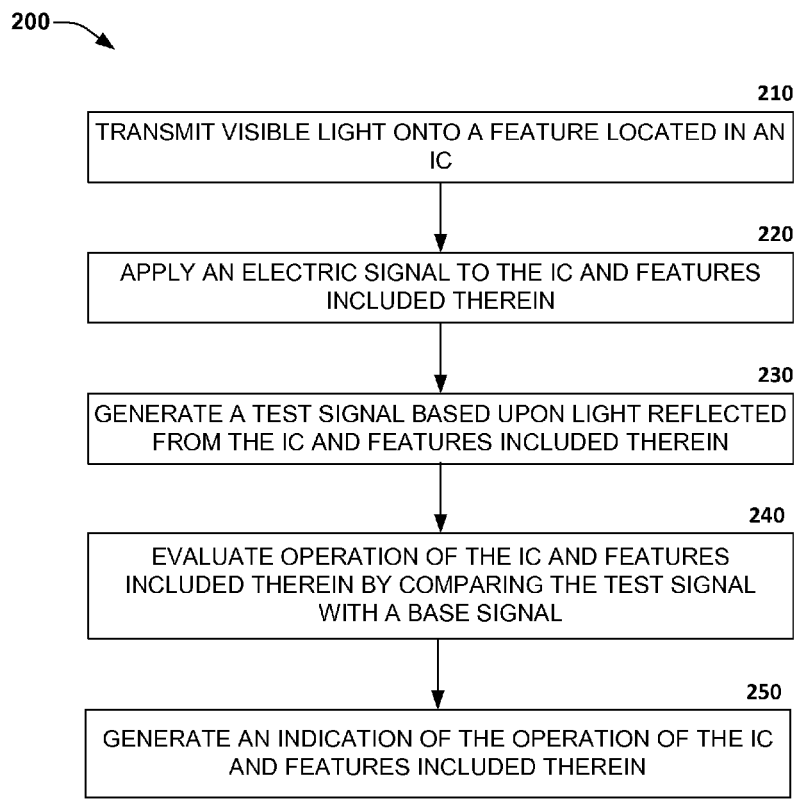
FIG. 2 is a flow diagram illustrating an exemplary methodology for utilizing visible light for laser voltage probing.
Figure 3:
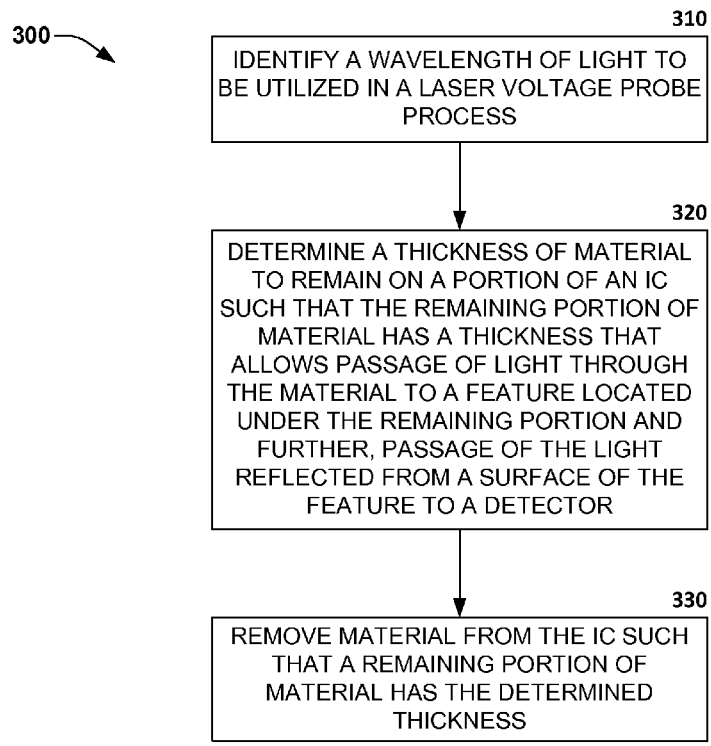
FIG. 3 is a flow diagram illustrating an exemplary methodology for thinning a device for analysis with laser voltage probing.

FIGS. 2 and 3 illustrate exemplary methodologies relating to utilizing visible light to determine operation of an IC device. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement the methodologies described herein FIG. 2 illustrates a methodology 200 for performing a LVP operation on an IC, wherein the LVP operation utilizes light from the visible portion of the electromagnetic spectrum. At 210, visible light is transmitted onto one or more features located in an IC. In an embodiment, the visible light is transmitted from a laser. The one or more features are covered with a layer of material included in the IC, e.g., a layer of semiconductor material such as silicon, wherein the semiconductor layer may include an insulating layer (e.g., a BOX layer). The layer of semiconductor material has been thinned from an original thickness to a thickness through which the visible light can travel from the laser to a surface of each feature in the one or more features that is visible to the light and the device remains functional.

At 220, an electrical signal is applied to the IC and the one or more features located in the IC. The electrical signal can be a clocked signal having a square wave profile. One or more interactions can occur between the light incident upon a feature and the electrical signal passing through it, wherein any light reflected from the surface of a feature undergoes modulation based in part upon the one or more interactions.

At 230, the reflected light is captured at a detector, wherein the detector is configured to generate a test signal based upon the reflected light, e.g., via optoelectronic conversion.

At 240, test signal can be received at a processing unit, wherein the processing unit can be configured to compare the test signal with a previously captured base signal. The base signal can be a signal captured for a known operation of the IC and features, for example, the base signal was captured during an LVP operation conducted on an IC having a known structure, operation, performance, etc. The base signal can also be obtained from a design file, or other suitable source. Comparison of the test signal with the base signal enables operation of the IC under test to be established and any further troubleshooting to be undertaken based thereon, e.g., determine whether any of the features included in the IC is defective.

At 250, an indication of operation of the IC, and included features, can be generated, wherein the indication can be a visual signal (e.g., a light), a data packet transmitted to another component which can act upon information contained in the data packet, presented on a display (e.g., with a defective feature such as a defective transistor identified).

FIG. 3 illustrates a methodology 300 for thinning a portion of an IC to facilitate examination with a LVP operation utilizing visible light. At 310, a wavelength of visible light for application in a LVP process is identified. For example, the visible light is generated by a laser and has a wavelength of 633 nm (e.g., the laser emits red light).

At 320, a thickness of material to remain on an IC after a thinning operation is performed is determined, wherein the material can be semiconductor material located on a backside of the IC (e.g., bulk silicon). The material to be thinned is located over a feature in the IC (e.g., a transistor), or across the entire IC, and the thickness of the material after thinning is such that a thinned portion of the material allows passage of the visible light through the portion of thinned material to the feature beneath. Further, the portion of material is thinned to enable passage of visible light reflected from a surface of a feature to pass through the thinned material and to be captured at a detector. For example, the thinned material has a thickness to enable double-through or round-trip transmission of the visible light through the thinned material. At an original thickness, the bulk silicon can absorb, refract, or reflect such a volume of the visible light during transmission to, and reflection from, the surface of the feature such that no discernible measure of any interaction(s) between the visible light incident upon the feature and an electrical signal at the feature can be discerned. However, by thinning the portion of material, the remaining material has a thickness that is sufficiently transparent to the visible light (e.g., incident light and reflected light) passing therethrough, and further the visible light retains any modulation imparted upon it during interaction with an electrical signal at the feature during an LVP operation.

At 330, the material is thinned to obtain the portion of thinned material having the determined thickness. The thinned material can have a thickness that is less than the determined thickness, the thickness can be such that the IC remains operational during the LVP operation. Any suitable process can be utilized to thin the material, where such processes include reactive ion-etching processing, FIB, gas-assisted FIB, pulse laser-assisted etching, $XeF_2$ etching, etc. Upon completion of the thinning operation, the IC can now be examined using the visible light-based LVP process.

Figure 4:
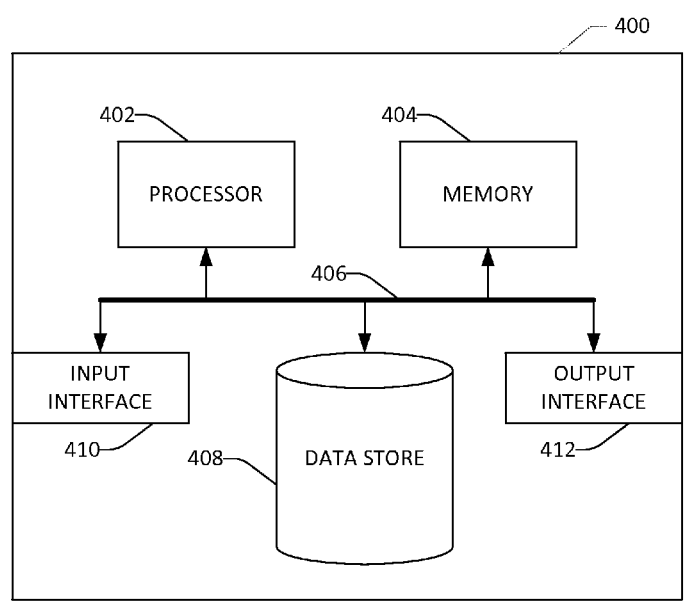
FIG. 4 illustrates an exemplary computing device.

Referring now to FIG. 4, a high-level illustration of an exemplary computing device 400 that can be used in accordance with the systems and methodologies disclosed herein is illustrated. For instance, the computing device 400 can be utilized to enable characterization of operation of one or more features included in an IC, wherein the IC has been thinned to facilitate LVP with visible light. For example, computing device 400 can operate as the processing unit 160. The computing device 400 includes at least one processor 402 that executes instructions that are stored in a memory 404. The instructions may be, for instance, instructions for implementing functionality described as being carried out by one or more components discussed above or instructions for implementing one or more of the methods described above. The processor 402 may access the memory 404 by way of a system bus 406. In addition to storing executable instructions, the memory 404 may also store operating parameters, required operating parameters, and so forth.

The computing device 400 additionally includes a data store 408 that is accessible by the processor 402 by way of the system bus 406. The data store 408 may include executable instructions, operating parameters, required operating parameters, etc. The computing device 400 also includes an input interface 410 that allows external devices to communicate with the computing device 400. For instance, the input interface 410 may be used to receive instructions from an external computer device, from a user, etc. The computing device 400 also includes an output interface 412 that interfaces the computing device 400 with one or more external devices. For example, the computing device 400 may display text, images, etc., by way of the output interface 412.

Additionally, while illustrated as a single system, it is to be understood that the computing device 400 may be a distributed system. Thus, for instance, several devices may be in communication by way of a network connection and may collectively perform tasks described as being performed by the computing device 400.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

What has been described above includes examples of one or more embodiments. It is, of course, not possible to describe every conceivable modification and alteration of the above structures or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A system comprising:
   a laser configured to emit visible light having a wavelength, wherein the visible light is transmitted to be incident upon an integrated circuit, and is reflected from a feature in the integrated circuit, wherein the feature is located beneath a layer of semiconductor material having a thickness to enable passage of the visible light through the semiconductor material during transmission of the visible light to the feature and reflection of the visible light from the feature, and further wherein the thickness of the layer of the semiconductor material is selected as a function of the wavelength of the visible light;
   a detector configured to generate a test signal based upon the visible light reflected from the integrated circuit feature;
   a processing unit; and
   memory that stores instructions that, when executed by the processing unit, cause the processing unit to perform acts comprising:
   receiving the test signal from the detector;
   comparing the test signal with a base signal, wherein the base signal is obtained from a test integrated circuit having a known condition;
   determining, based upon comparing the test signal with the base signal, a state of the integrated circuit, wherein the state identifies one or more differences between the test signal and the base signal; and
   generating an output that is indicative of the state of the integrated circuit feature.

2. The system of claim 1, wherein the semiconductor material has been thinned from an original thickness to the thickness to enable passage of the visible light through the semiconductor material during transmission of the visible light to the feature and reflection of the visible light from the feature.

3. The system of claim 2, wherein the semiconductor material has been thinned by at least one of reactive ion-etching processing, focused ion beam, pulse laser-assisted chemical etching, or xenon difluoride etching.

4. The system of claim 2, wherein the semiconductor material has been thinned to expose a buried oxide layer located between the laser and the feature.

5. The system of claim 2, wherein removal of the semiconductor material does not interfere with operation of the integrated circuit.

6. The system of claim 2, wherein the semiconductor material has been thinned to a thickness of about 2-4 microns, of about 3-4 microns, of about 2 microns, of about 0.25 microns, of about 60-70 nanometers, or a distance of 2-4 times a wavelength of the incident visible light, between an exposed surface of the semiconductor material and a surface of the feature.

7. The system of claim 2, wherein the semiconductor material has been thinned to enable passage of the visible light through the semiconductor during transmission of the visible light to the feature and reflection of the visible light from the feature.

8. The system of claim 1, wherein the feature is at least one of a transistor, a diode, a PN junction, or a semiconductor device.

9. The system of claim 1, wherein the visible light has a wavelength of about 650 nanometers (nm), of about 510 nm, of about 475 nm, a value in a range of about 400-700 nm, a value in a range of about 620-750 nm, a value in a range of about 495-570 nm, a value in a range of about 450-495 nm, or a value in a range of about 633-640 nm.

10. The system of claim 1, further comprising a signal source that is configured to energize the feature with an electrical signal, wherein during incidence of the visible light on the integrated circuit feature the electrical signal at the integrated circuit feature interacts with the incident visible light such that the incident visible light has at least one characteristic different to the reflected visible light.

11. A method comprising:
    illuminating an integrated circuit (IC) with visible light having a wavelength, wherein the visible light is incident upon a feature in the IC and is reflected from the feature, wherein the feature is located beneath a layer of semiconductor material having a thickness enabling passage of the visible light through the semiconductor material during transmission of the visible light to the feature and reflection of the visible light from the feature, wherein the thickness of the semiconductor material is selected based upon the wavelength of the visible light, and further wherein the visible light is generated by a laser;

applying an electrical signal to the feature, wherein the electrical signal modifies the visible light incident upon the feature;

capturing the visible light reflected from the feature, wherein the reflected visible light is captured by a detector;

generating a test signal based upon the visible light reflected from the feature, wherein the test signal is generated by the detector;

comparing the test signal with a base signal, wherein the base signal is obtained from a test integrated circuit having a known condition, wherein the comparing is performed by a processing unit that is in communication with the detector;

determining, based upon the comparing of the test signal with the base signal, a state of the feature, wherein the determining is performed by the processing unit; and generating an output indicative of the state of the feature, wherein the output is generated by the processing unit.

12. The method of claim 11, further comprising thinning the semiconductor material from an original thickness to the thickness enabling passage of the visible light through the semiconductor material during transmission of the visible light to the feature and reflection of the visible light from the feature.

13. The method of claim 12, wherein the semiconductor material has been thinned by at least one of reactive ion-etching processing, focused ion beam, pulse laser-assisted etching, or xenon difluoride etching.

14. The method of claim 11, wherein the semiconductor material has been thinned to a thickness of about 2-4 microns, of about 3-4 microns, of about 2 microns, of about 0.25 microns, of about 60-70 nanometers, of about 5 nanometers, or a distance of 2-4 times a wavelength of the incident visible light, between an exposed surface of the semiconductor material and a surface of the feature.

15. The method of claim 11, wherein the feature is at least one of a transistor, a diode, a PN junction, or a semiconductor device.

16. The method of claim 11, wherein the visible light has a wavelength of about 650 nanometers (nm), of about 510 nm, of about 475 nm, a value in a range of about 400-700 nm, a value in a range of about 620-750 nm, a value in a range of about 495-570 nm, a value in a range of about 450-495 nm, or a value in a range of about 633-640 nm.

17. A system comprising:
a laser configured to emit visible light having a wavelength, wherein the visible light is transmitted to be incident upon an integrated circuit, and is reflected from a feature in the integrated circuit, wherein the feature is located beneath a layer of buried oxide material having a thickness to enable passage of the visible light through the buried oxide material during transmission of the visible light to the feature and reflection of the visible light from the feature, and further wherein the thickness of the buried oxide material is selected based upon the wavelength of the visible light;

a detector configured to generate a test signal based upon the visible light reflected from the feature;

a processing unit; and memory that stores instructions that, when executed by the processing unit, cause the processing unit to perform acts comprising:
comparing the test signal with a base signal, wherein the base signal is obtained from a test integrated circuit having a known condition;
determining, based upon comparing the test signal with the base signal, a state of the feature; and
generating an output that is indicative of the state of the feature.

18. The system of claim 17, wherein the buried oxide material has been thinned to a thickness of about 2-4 microns, of about 3-4 microns, of about 2 microns, of about 0.25 microns, of about 60-70 nanometers, or a distance of 2-4 times a wavelength of the incident visible light, between an exposed surface of the semiconductor material and the transistor surface.

19. The system of claim 17, wherein the visible light has a wavelength of about 650 nanometers (nm), of about 510 nm, of about 475 nm, a value in a range of about 400-700 nm, a value in a range of about 620-750 nm, a value in a range of about 495-570 nm, a value in a range of about 450-495 nm, or a value in a range of about 633-640 nm.

20. The system of claim 17, wherein the feature is at least one of a transistor, a diode, a PN junction, or a semiconductor device.

* * * * *